(12) United States Patent
Shellenberger

(10) Patent No.: US 11,607,227 B2
(45) Date of Patent: *Mar. 21, 2023

(54) SURGICAL CLIP AND CLIP APPLIER

(71) Applicant: TELEFLEX MEDICAL INCORPORATED, Morrisville, NC (US)

(72) Inventor: Carson J. Shellenberger, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 526 days.

This patent is subject to a terminal disclaimer.

(21) Appl. No.: 15/927,774

(22) Filed: Mar. 21, 2018

(65) Prior Publication Data

US 2018/0271532 A1 Sep. 27, 2018

Related U.S. Application Data

(60) Provisional application No. 62/474,538, filed on Mar. 21, 2017, provisional application No. 62/627,536, filed on Feb. 7, 2018.

(51) Int. Cl.
*A61B 17/122* (2006.01)
*A61B 17/128* (2006.01)
*A61B 17/00* (2006.01)

(52) U.S. Cl.
CPC .......... *A61B 17/122* (2013.01); *A61B 17/128* (2013.01); *A61B 17/1227* (2013.01); *A61B 17/1285* (2013.01); *A61B 2017/00477* (2013.01)

(58) Field of Classification Search
CPC .............. A61B 17/122; A61B 17/1285; A61B 2017/00477; A61B 17/1227; A61B 17/0487; A61B 17/128
See application file for complete search history.

(56) References Cited

U.S. PATENT DOCUMENTS 929,868 A 12/1899 Mueller
1,482,290 A 1/1924 Elzi
(Continued)

FOREIGN PATENT DOCUMENTS

CN 1356092 A 7/2002
CN 1846638 A 10/2006
(Continued)

OTHER PUBLICATIONS

International Search Report and Written Opinion issued in PCT/US2018/023600, dated Jun. 4, 2018.
(Continued)

*Primary Examiner* — Melanie R Tyson
*Assistant Examiner* — Rachel S Highland
(74) *Attorney, Agent, or Firm* — BakerHostetler

(57) ABSTRACT

A clip applier assembly may include a surgical clip and a clip applier. The surgical clip may include first and second leg members configured to ligate tissue. The first leg member may include a first proximal portion, a first distal portion, a first inner surface, and a first outer surface. The first outer surface may have a convex curvature. The second leg member may include a second proximal portion, a second distal portion, a second inner surface, and a second outer surface. The second leg member may further include an inner portion and an outer portion separated by a channel. The second outer surface may be formed on the outer portion and have a convex curvature. The clip applier may have a first jaw member configured to engage the first outer surface and a second jaw member configured to engage the second outer surface.

27 Claims, 7 Drawing Sheets

(56) References Cited

U.S. PATENT DOCUMENTS

| | | |
|---|---|---|
| 1,728,322 A | 9/1929 | Badrian |
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Bay |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,446,212 A | 5/1969 | Le Roy |
| 3,463,156 A | 8/1969 | Mcdermott |
| 3,503,396 A | 3/1970 | Pierie |
| 3,503,397 A | 3/1970 | Fogarty |
| 3,503,398 A | 3/1970 | Fogarty |
| 3,766,925 A | 10/1973 | Rubricius |
| 3,825,012 A | 7/1974 | Nicoll |
| 3,827,438 A | 8/1974 | Kees, Jr. |
| 3,867,944 A | 2/1975 | Samuels |
| 3,874,042 A | 4/1975 | Eddleman et al. |
| 3,954,108 A | 5/1976 | Davis |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,345,600 A | 8/1982 | Rothfuss |
| 4,346,869 A | 8/1982 | MacNeill |
| 4,390,019 A | 6/1983 | LeVeen et al. |
| 4,394,864 A | 7/1983 | Sandhaus |
| 4,414,721 A | 11/1983 | Hufnagel |
| 4,418,694 A | 12/1983 | Beroff et al. |
| 4,428,374 A | 1/1984 | Auburn |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di Giovanni et al. |
| 4,492,232 A | 1/1985 | Green |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A | 10/1986 | Golden |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A * | 10/1991 | Schmidt ............ A61B 17/1227 606/157 |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank, III et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | McQuilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,797,922 A | 8/1998 | Hessel et al. |
| 5,810,853 A | 9/1998 | Yoon |
| 5,843,097 A | 12/1998 | Mayenberger et al. |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,997,548 A | 12/1999 | Jahanger |
| 6,010,516 A | 1/2000 | Hulka |
| 6,013,088 A | 1/2000 | Karavidas |
| 6,015,417 A | 1/2000 | Reynolds, Jr. |
| 6,050,996 A | 4/2000 | Schmaltz et al. |
| 6,131,576 A | 10/2000 | Davis |
| 6,210,419 B1 | 4/2001 | Mayenberger et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,558,408 B1 | 5/2003 | Fogarty et al. |

(56) References Cited

U.S. PATENT DOCUMENTS

| | | |
|---|---|---|
| 6,599,298 B1 | 7/2003 | Forster et al. |
| 6,695,854 B1 | 2/2004 | Kayan et al. |
| 6,699,258 B1 | 3/2004 | Sadler et al. |
| 6,719,766 B1 | 4/2004 | Buelna et al. |
| 6,773,438 B1 | 8/2004 | Knodel et al. |
| 6,780,195 B2 | 8/2004 | Porat |
| 6,814,742 B2 | 11/2004 | Kimura et al. |
| 6,824,547 B2 | 11/2004 | Wilson, Jr. et al. |
| 6,837,895 B2 | 1/2005 | Mayenberger |
| 6,843,253 B2 | 1/2005 | Parkes |
| 6,863,675 B2 | 3/2005 | Wilson, Jr. |
| 6,880,699 B2 | 4/2005 | Gallagher |
| 6,926,712 B2 | 8/2005 | Phan |
| 6,932,816 B2 | 8/2005 | Phan |
| 6,989,017 B2 | 1/2006 | Howell et al. |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,131,977 B2 | 11/2006 | Fowler |
| 7,179,265 B2 | 2/2007 | Manetakis et al. |
| 7,211,091 B2 | 5/2007 | Fowler et al. |
| 7,211,092 B2 | 5/2007 | Hughett |
| 7,261,724 B2 | 8/2007 | Molitor et al. |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,357,805 B2 | 4/2008 | Masuda et al. |
| 7,402,164 B2 | 7/2008 | Watson, Jr. et al. |
| 7,572,266 B2 | 8/2009 | Young et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,648,514 B1 | 1/2010 | Nakao |
| 7,727,231 B2 | 6/2010 | Swanson |
| 7,753,908 B2 | 7/2010 | Swanson |
| 7,785,324 B2 | 8/2010 | Eberl |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,142,451 B2 | 3/2012 | Boulnois et al. |
| 8,262,639 B2 | 9/2012 | Mathias |
| 8,403,138 B2 | 3/2013 | Weisshaupt et al. |
| 8,425,412 B2 | 4/2013 | Rucker |
| 8,465,507 B2 | 6/2013 | Cosgrove et al. |
| 8,512,357 B2 | 8/2013 | Viola |
| 8,585,718 B2 | 11/2013 | Disch et al. |
| 8,764,774 B2 | 7/2014 | Sigmon, Jr. |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,737,309 B1 | 8/2017 | Ad |
| 9,855,053 B2 | 1/2018 | Bagaoisan et al. |
| 9,901,352 B2 | 2/2018 | Fago et al. |
| 9,955,977 B2 | 5/2018 | Martinez et al. |
| 10,064,623 B2 | 9/2018 | Soutorine et al. |
| 10,136,898 B2 | 11/2018 | Schmidt et al. |
| 10,285,712 B2 | 5/2019 | Cosgrove, III et al. |
| 10,292,712 B2 | 5/2019 | Shankarsetty |
| 10,307,166 B2 | 6/2019 | Willett et al. |
| 10,383,637 B2 | 8/2019 | Castro |
| 10,758,243 B2 | 9/2020 | Salas |
| 10,925,616 B2 | 2/2021 | Shellenberger et al. |
| 11,160,559 B2 | 11/2021 | Shellenberger |
| 11,266,408 B2 | 3/2022 | Shellenberger |
| 2002/0046961 A1 | 4/2002 | Levinson et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0014060 A1 | 1/2003 | Wilson et al. |
| 2003/0074009 A1 | 4/2003 | Ramsey et al. |
| 2003/0158548 A1 | 8/2003 | Phan et al. |
| 2004/0010272 A1 | 1/2004 | Manetakis et al. |
| 2004/0040875 A1 | 3/2004 | Gallagher |
| 2004/0059359 A1 | 3/2004 | Wilson, Jr. |
| 2004/0097970 A1 | 5/2004 | Hughett |
| 2004/0172043 A1* | 9/2004 | Watson, Jr. ...... A61B 5/150038<br>606/120 |
| 2005/0090838 A1 | 4/2005 | Sixto, Jr. et al. |
| 2005/0149063 A1 | 7/2005 | Young et al. |
| 2005/0149068 A1 | 7/2005 | Williams et al. |
| 2005/0149069 A1 | 7/2005 | Bertolero et al. |
| 2005/0165421 A1 | 7/2005 | Wilson, Jr. et al. |
| 2005/0165422 A1 | 7/2005 | Wilson |
| 2005/0165423 A1 | 7/2005 | Gallagher et al. |
| 2005/0165429 A1 | 7/2005 | Douglas et al. |
| 2005/0171560 A1 | 8/2005 | Hughett |
| 2005/0234478 A1 | 10/2005 | Wixey et al. |
| 2005/0240219 A1 | 10/2005 | Kahle et al. |
| 2005/0277959 A1 | 12/2005 | Cosgrove et al. |
| 2006/0217749 A1 | 9/2006 | Wilson et al. |
| 2007/0016228 A1 | 1/2007 | Salas |
| 2007/0083218 A1 | 4/2007 | Morris |
| 2007/0118161 A1 | 5/2007 | Kennedy et al. |
| 2007/0149989 A1 | 6/2007 | Santilli et al. |
| 2007/0276417 A1 | 11/2007 | Mendes, Jr. et al. |
| 2007/0282355 A1 | 12/2007 | Brown et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0112233 A1 | 4/2009 | Xiao |
| 2009/0171380 A1 | 7/2009 | Whiting |
| 2009/0240266 A1 | 9/2009 | Dennis |
| 2010/0057107 A1 | 3/2010 | Sorrentino et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274262 A1 | 10/2010 | Schulz et al. |
| 2010/0274264 A1 | 10/2010 | Schulz et al. |
| 2010/0274268 A1 | 10/2010 | Singh et al. |
| 2011/0022079 A1 | 1/2011 | Miles et al. |
| 2011/0087244 A1 | 4/2011 | Weisshaupt et al. |
| 2011/0144665 A1 | 6/2011 | Malkowski |
| 2011/0245848 A1 | 10/2011 | Rosenberg et al. |
| 2011/0295291 A1 | 12/2011 | Trivisani |
| 2012/0027765 A1 | 2/2012 | Jackson et al. |
| 2012/0074200 A1 | 3/2012 | Schmid et al. |
| 2012/0083803 A1 | 4/2012 | Patel et al. |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0006271 A1 | 1/2013 | Vold et al. |
| 2013/0226200 A1 | 8/2013 | Kappel et al. |
| 2013/0245651 A1* | 9/2013 | Schmidt ............ A61B 17/122<br>606/157 |
| 2013/0245652 A1 | 9/2013 | Cosgrove et al. |
| 2013/0261642 A1 | 10/2013 | Willett et al. |
| 2014/0018830 A1 | 1/2014 | Shelton |
| 2014/0058411 A1 | 2/2014 | Soutorine et al. |
| 2014/0207156 A1 | 7/2014 | Malkowski |
| 2014/0243862 A1 | 8/2014 | Bagaoisan et al. |
| 2014/0309677 A1 | 10/2014 | Baldwin |
| 2015/0066057 A1 | 3/2015 | Rockrohr et al. |
| 2015/0136835 A1 | 5/2015 | Shelton, IV et al. |
| 2015/0190137 A1 | 7/2015 | Salas |
| 2015/0320426 A1 | 11/2015 | Cosgrove et al. |
| 2016/0174981 A1 | 6/2016 | Fago et al. |
| 2016/0270790 A1 | 9/2016 | Jankowski |
| 2016/0354089 A1 | 12/2016 | Whiting |
| 2017/0014135 A1 | 1/2017 | Martin et al. |
| 2017/0238935 A1 | 8/2017 | Shi |
| 2018/0036008 A1 | 2/2018 | Ramsey et al. |
| 2018/0168659 A1 | 6/2018 | Bagaoisan et al. |

(56) References Cited

U.S. PATENT DOCUMENTS

| | | |
|---|---|---|
| 2018/0271527 A1 | 9/2018 | Shellenberger |
| 2018/0271534 A1 | 9/2018 | Shellenberger |
| 2018/0271535 A1 | 9/2018 | Shellenberger et al. |
| 2018/0271536 A1 | 9/2018 | Shellenberger et al. |
| 2021/0128159 A1 | 5/2021 | Taylor et al. |
| 2022/0047271 A1 | 2/2022 | Shellenberger |

FOREIGN PATENT DOCUMENTS

| | | |
|---|---|---|
| CN | 101543418 A | 9/2009 |
| CN | 103442658 A | 12/2013 |
| CN | 105054989 A | 11/2015 |
| CN | 105078536 A | 11/2015 |
| CN | 106037947 A | 10/2016 |
| CN | 106264646 A | 1/2017 |
| EP | 0086640 A2 | 8/1983 |
| EP | 0201344 A2 | 11/1986 |
| EP | 0314064 A2 | 5/1989 |
| EP | 1233705 A2 | 8/2002 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| JP | 56151034 A | 11/1981 |
| JP | 61-007818 B2 | 3/1986 |
| JP | 61259652 A | 11/1986 |
| JP | 3178648 A | 8/1991 |
| JP | 05-200039 A | 8/1993 |
| JP | 2002345828 A | 12/2002 |
| JP | 2004-522468 A | 7/2004 |
| JP | 2004-535236 A | 11/2004 |
| JP | 4263594 B2 | 5/2009 |
| JP | 2011-517423 A | 6/2011 |
| JP | 2014-531250 A | 11/2014 |
| JP | 2015-043977 A | 3/2015 |
| WO | 9738634 A1 | 10/1997 |
| WO | 0135837 A1 | 5/2001 |
| WO | 2004043225 A2 | 5/2004 |
| WO | 2005/107613 A1 | 11/2005 |
| WO | 2006102578 A1 | 9/2006 |
| WO | 2012075532 A1 | 6/2012 |
| WO | 2013040467 A2 | 3/2013 |
| WO | 2016094647 A1 | 6/2016 |
| WO | 2018/175626 A1 | 9/2018 |
| WO | 2020/018784 A1 | 1/2020 |

OTHER PUBLICATIONS

Office Action received for Japanese Patent Application No. 2019-552082 dated Oct. 19, 2020, 4 pages (English Translation).
Office Action received for Japanese Patent Application No. 2019-552082, dated Apr. 28, 2021, 3 pages (English Translation).
Supplementary European Search Report received for EP Patent Application No. 18772298, dated Sep. 1, 2020, 10 pages.

\* cited by examiner

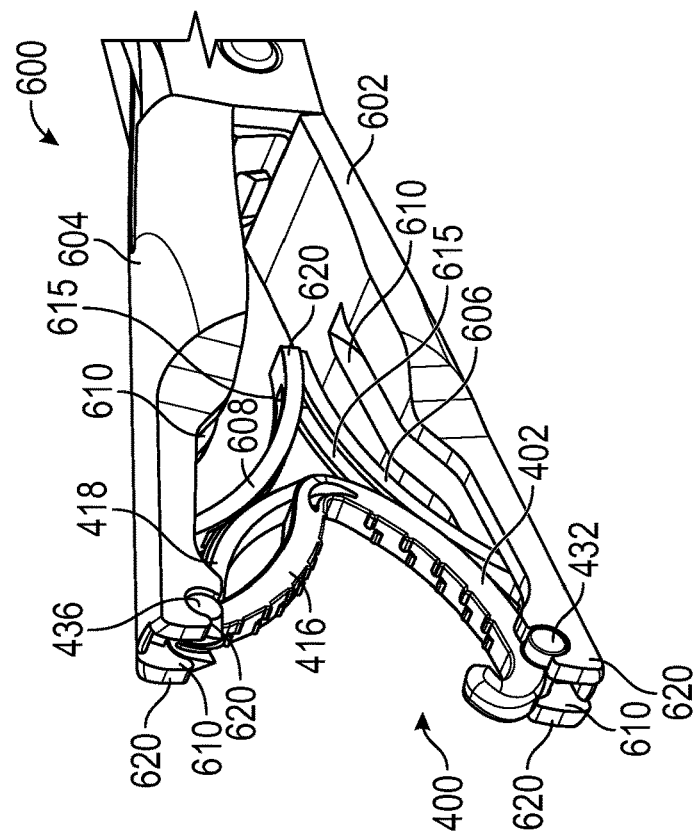
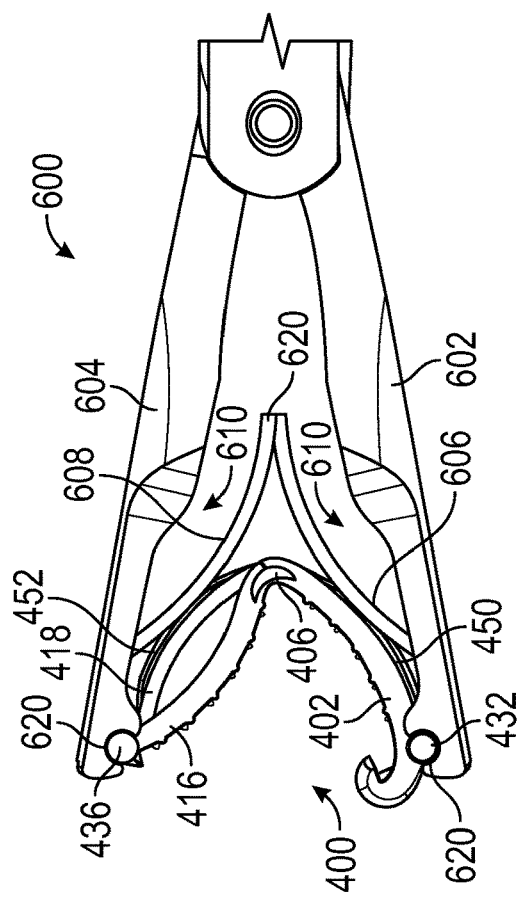
FIG. 6B
FIG. 6A

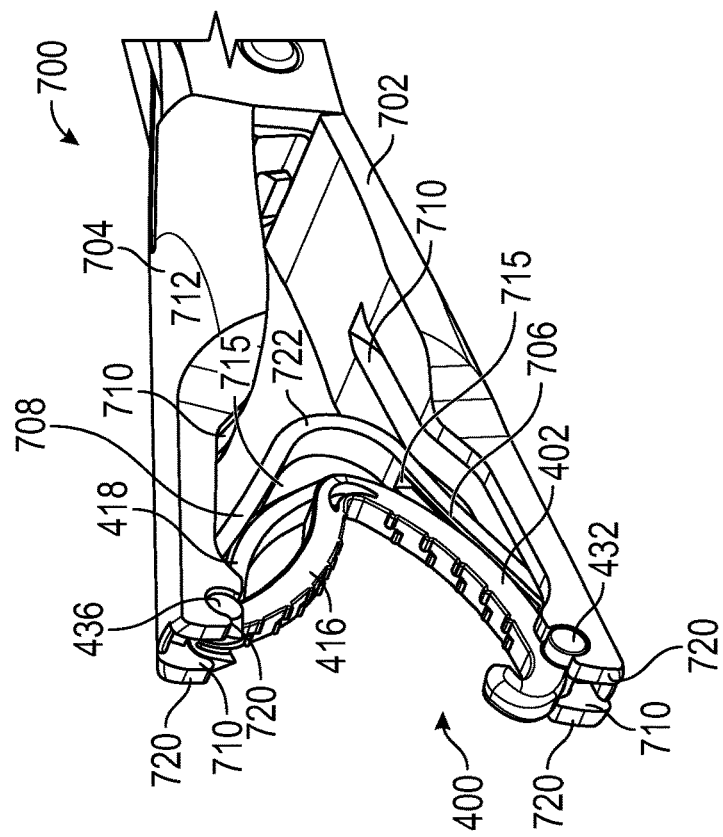
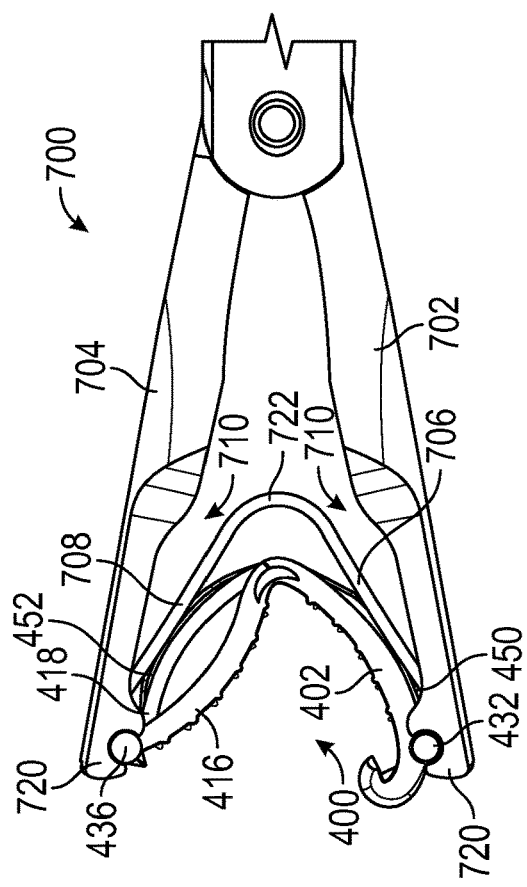
FIG. 7B
FIG. 7A

SURGICAL CLIP AND CLIP APPLIER

PRIORITY

The present Non-Provisional Patent Application claims priority to U.S. Provisional Patent Application No. 62/474,538, filed on Mar. 21, 2017, and U.S. Provisional Patent Application No. 62/627,536, filed on Feb. 7, 2018, the entirety of the disclosures of which are incorporated herein by reference.

TECHNICAL FIELD

The present disclosure relates generally to surgical clips and clip appliers, and more particularly, to surgical clips and clip appliers with improved stability.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventor recognizes that there is a need to improve one or more features of the surgical clips, such as stability of the surgical clip in a clip applier. Current clip appliers often secure the surgical clip at two points of contact provided by bosses at distal ends of leg members of the surgical clip. However, the bosses do not provide sufficient stability to the surgical clip, which can move relative to the clip applier during a surgical procedure, or even fall out of the jaw members. For example, the surgical clip can fish-tail when received between jaw members not providing sufficient stability along the length of the surgical clip. Current surgical clips are also difficult to feed through the shaft of an automatic clip applier. The disclosed devices and methods are directed to mitigating or overcoming one or more of the problems set forth above and/or other problems in the prior art.

A first aspect is directed to a surgical clip configured to ligate tissue. The surgical clip may include a first leg member having a first proximal portion, a first distal portion, a first inner surface, and a first outer surface. The first outer surface may have a convex curvature. The surgical clip may also include a second leg member having a second proximal portion, a second distal portion, a second inner surface, and a second outer surface. The second leg member may further include an inner portion and an outer portion separated by a channel. The second outer surface may be formed on the outer portion and have a convex curvature.

In some embodiments, the inner portion and the outer portion may be formed integrally. In some embodiments, the inner portion and the outer portion may include a polymer. In some embodiments, the outer portion may extend at least a quarter of a length of the second leg member. In some embodiments, the outer portion may extend at least half of the length of the second leg member. In some embodiments, the outer portion may extend substantially the entire length of the second leg member. In some embodiments, a width of the outer portion may be smaller than a width of the inner portion. In some embodiments, the convex curvature of the second outer surface may extend from a proximal end of the outer portion to a distal end of the outer portion. In some embodiments, the first outer surface may have a first longitudinal protrusion, and the second outer surfaces may have a second longitudinal protrusion. In some embodiments, the surgical clip may further have a hook member on a distal portion of one of the first and second leg members, and a tip member on another of the first and second leg members, the hook member being configured to receive the tip member in a closed configuration. In some embodiments, the hook member may be on the first leg member, and the tip member may be on the second leg member. In some embodiments, at least one tooth may be on the first inner surface, and at least one tooth may be on the second inner surface. In some embodiments, the first inner surface may include a concave curvature, and the second inner surface may include a convex curvature.

A second aspect is directed to a surgical clip configured to ligate tissue. The surgical clip may include a first leg member having a first proximal portion, a first distal portion, a first inner surface, and a first outer surface. The first inner surface may have a concave curvature, and the first outer surface may have a convex curvature. The surgical clip may include a second leg member including a second proximal portion, a second distal portion, a second inner surface, and a second outer surface. The second leg member may further include an inner portion and an outer portion separated by a channel. The second inner surface may be formed on the inner portion portion and have a convex curvature, and the second outer surface may be formed on the outer portion and have a convex curvature. The inner portion and the outer portion may be integrally formed of a polymer, and the outer portion may extend at least a quarter of a length of the second leg member. A hook member may be on the first distal portion of the first leg member, and a tip member may be on the second distal portion of the second leg member. The hook member may be configured to deflect around the tip member to secure the surgical clip in a closed configuration. A hinge member may pivotably couple the first proximal portion and the second proximal portion.

A third aspect is directed to a clip applier system configured to ligate tissue. The clip applier system may include a surgical clip and a clip applier having a first jaw member and a second jaw member. The surgical clip may include first and second leg members. The first leg member may have a proximal portion, a distal portion, a first inner surface, and a first outer surface. The first outer surface may have a convex curvature engaging the first jaw member. The second leg member may have a proximal portion, a distal portion, a second inner surface, and a second outer surface. The second leg member may further have an inner portion and an outer portion separated by a channel. The second inner surface may be formed on the inner portion, and the second outer surface may be formed on the outer portion and have a convex curvature engaging the second jaw member.

In some embodiments, the clip applier may include a first flexible member engaging the first leg member and a second flexible member engaging the second leg member. In some embodiments, the first flexible member may be biased into engagement with the first outer surface, and the second flexible member may be biased into engagement with the second outer surface. In some embodiments, a portion of the first flexible member may be received within a channel of the first jaw member, and a portion of the second flexible member may be received within a channel of the second jaw member. In some embodiments, a distal portion of the first flexible member may be secured to the first jaw member, and a distal portion of the second flexible member may be secured to the second jaw member. In some embodiments, a proximal portion of the first flexible member and a proximal portion of the second flexible member may be spaced apart. In some embodiments, a proximal portion of the first flexible member and a proximal portion of the second flexible member are joined or integral. In some embodiments, the first leg member may have a first longitudinal protrusion configured to be received in a first slot of the first jaw member, and the second leg member may have a second longitudinal protrusion configured to be received in a second slot of the second jaw member.

A fourth aspect is directed to a method of loading a clip applier with a surgical clip. The clip applier may include a first jaw member and a second jaw member, and the surgical clip may include a first leg member and a second leg member. The first leg member may have a first proximal portion, a first distal portion, a first inner surface, and a first outer surface, and the first outer surface may have a convex curvature. The second leg member may have a second proximal portion, a second distal portion, a second inner surface, and a second outer surface. The second leg member may further have an inner portion and an outer portion separated by a channel, the second outer surface being formed on the outer portion and having a convex curvature. The method may include receiving the surgical clip between the first jaw member and the second jaw member, engaging the convex curvature of the first outer surface with the first jaw member, and engaging the convex curvature of the second outer surface with the second jaw member.

BRIEF DESCRIPTION OF THE DRAWINGS

In order that the disclosure may be readily understood, aspects of this disclosure are illustrated by way of examples in the accompanying drawings.

FIG. 6A illustrates a side view of an exemplary embodiment of a third manual clip applier loaded with the surgical clip of FIG. 4.

FIG. 6B illustrates a perspective view the exemplary manual clip applier of FIG. 6A.

FIG. 7A illustrates a side view of an exemplary embodiment of a fourth manual clip applier loaded with the surgical clip of FIG. 4.

FIG. 7B illustrates a perspective view of the manual clip applier of FIG. 7A.

The same or similar reference numbers may be used in the drawings and the following detailed description to refer to the same or similar parts.

DETAILED DESCRIPTION

Figure 1A:
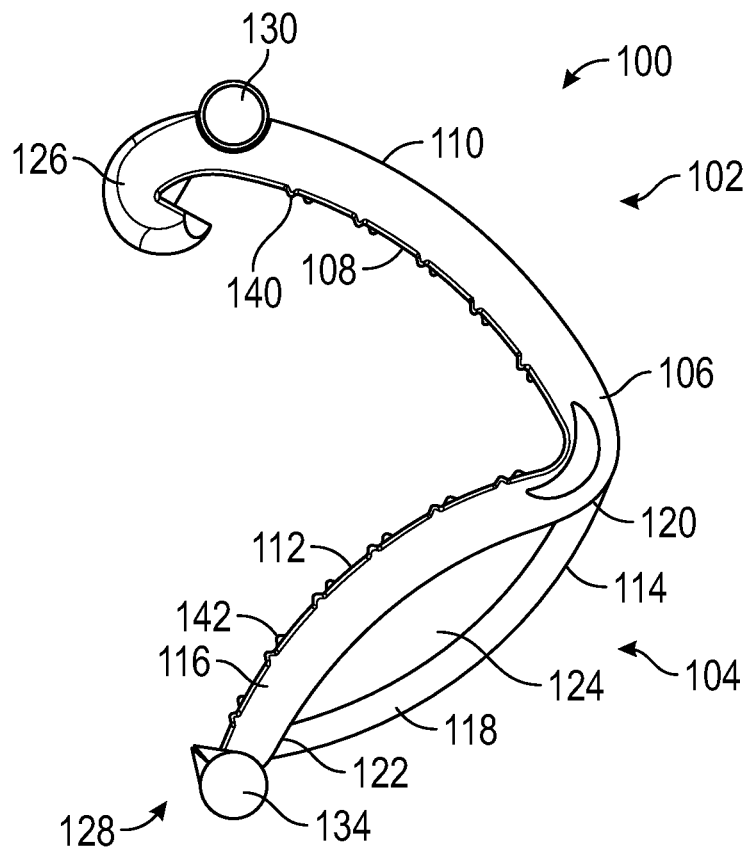
FIG. 1A illustrates a side view of a first exemplary embodiment of a surgical clip in an exemplary open configuration according to the present disclosure.

The invention will now be described with reference to the figures, in which like reference numerals may refer to like parts throughout. In accordance with conventional practice, as used herein, and unless otherwise indicated herein, the term "proximal portion" refers to the specified portion of a component which is generally closer to the medical personnel handling or manipulating the device as it is intended to be used, and the term "distal portion" refers to the specified portion of a component which is opposite the proximal portion. The term "longitudinal" is directed to the dimension which extends along the length of the component from the proximal portion to the respective distal portion. The "transverse" direction is directed to any axis or direction which is orthogonal to the longitudinal lengths of the component. Accordingly, the term "length" refers to a dimension of the component along the longitudinal direction. The term "height" or "vertical" refers to a dimension of the component along a compression direction of the clip applier and/or surgical clip. The term "thickness" refers to the dimension between opposing edges of component along the compression or vertical direction. The term "width" refers to a dimension of the components in a lateral direction substantially transverse to the length and the height. The term "concave" and "convex" refers to the curvature of a surface or component visible when viewing an exterior of the surface or component. Similar terminology is used throughout the written disclosure.

The present invention is generally directed to surgical clips and/or clip appliers that may be used in medical procedures, such as ligating tissue. The surgical clips and/or clip appliers may include improved retention mechanisms that reduce relative movement of the surgical clip when being applied by the clip applier. A leg member of the surgical clip may include an inner portion (e.g., an inner rib) and an outer portion (e.g., an outer rib) separated by a channel. Each leg member of the surgical clip may have an outer surface having a convex curvature that increases a contact area between the surgical clip and the clip applier. The clip applier may have one or more flexible members that receive and/or engage the outer surfaces of the surgical clip, such as the outer surface of the outer portion. The flexible members may be disposed on each of the jaw members of the clip applier to engage respective leg members of the surgical clip. The flexible members may be a spring-based metal (e.g., spring steel) that is biased to receive and/or engage the leg members of the surgical clip. The flexible members may be compressed when the clip applier compresses the surgical clip onto tissue. The flexible members may also be configured to nest into longitudinal channels of the first and second jaw members as the clip applier closes to enable full closure of the surgical clip. In some embodiments, the outer surface of the surgical clip may include a longitudinal protrusion configured to be received in a longitudinal slot of the flexible members to reduce lateral movement of the surgical clip.

Figure 1B:
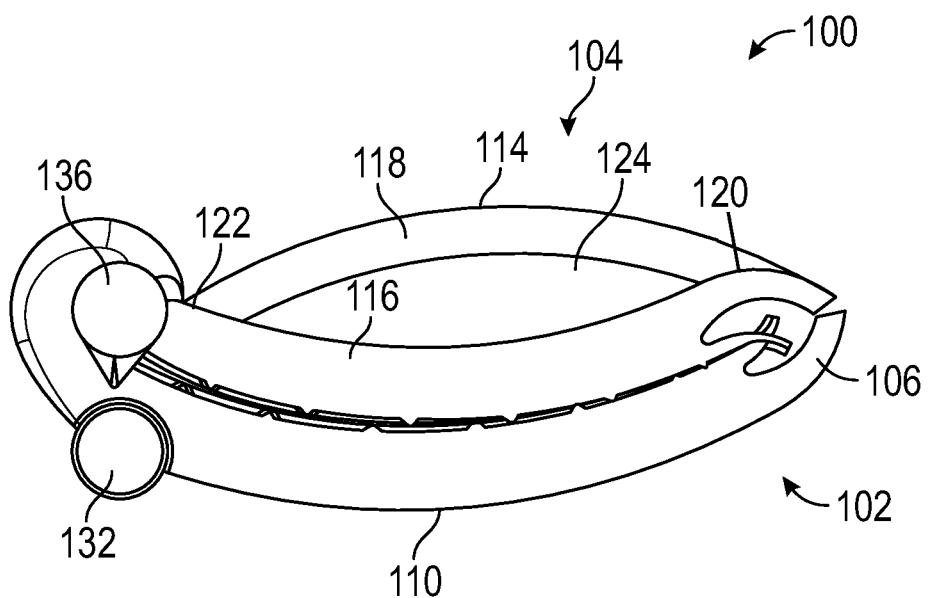
FIG. 1B illustrates a side view of the surgical clip of FIG. 1A in an exemplary closed configuration.

FIG. 1A illustrates a side view of a surgical clip 100 in an open configuration, and FIG. 1B illustrates a side view of the surgical clip 100 in a closed configuration. As illustrated, the surgical clip 100 may have a proximal portion and a distal portion. The surgical clip 100 may further include a first leg member 102 having a proximal portion and a distal portion, and a second leg member 104 having a proximal portion and a distal portion. The first and second lee members 102, 104 may be integrally joined at the proximal portions by a hinge member 106.

The first and second leg members 102, 104 may include surfaces having curved portions. For example, the first leg member 102 may include a first inner surface 108 and a first outer surface 110, and the second leg member 104 may include a second inner surface 112 and a second outer surface 114. As shown in FIG. 1A, the first inner surface 108 may have a concave curvature, and the first outer surface 110 may have a convex curvature. The second inner surface 112 may have a convex curvature, and the second outer surface 114 may have a convex curvature. The concave curvature of the first inner surface 108 and/or the convex curvature of the first outer surface 110 may extend substantially the entire length of the first leg member 102. The convex curvature of the second inner surface 112 and/or the convex curvature of the second outer surface 114 may extend substantially the entire length of the second leg member 104. The inner surfaces 108, 112 may be approximated or contact in a closed configuration. The first leg member 102 may also include opposing side surfaces (projecting into and out of the page of FIGS. 1A-B), and the second leg member 104 may include opposing side surfaces (projecting into and out of the page of FIGS. 1A-B).

The second leg member 104 may include an inner portion 116 (e.g., an inner rib) and an outer portion 118 (e.g., an outer rib) integrally joined at a proximal portion 120 and a distal portion 122. The inner portion 116 may form at least a portion of the second inner surface 112 and have an outer surface with a concave curvature, and the outer portion 118 may form at least a portion of the second outer surface 114 and have an inner surface with a concave curvature. The curvature of the inner portion 116 and/or outer portion 118 may extend from a proximal end (e.g., proximal portion 120) to a distal end (e.g., distal portion 122) of the respective inner and outer portion 116, 118. At least one of the inner portion 116 and the outer portion 118 may have a thickness less than a thickness of the first leg member 102. The smaller thickness of the inner portion 116 and/or outer portion 118 may provide more flexibility to allow deflection of the second inner surface 112 to different thicknesses of tissue. The inner portion 116, the outer portion 118, and/or the first leg member 102 may have substantially the same radius of curvature. The surgical clip 100 may have a generally symmetric outer profile along the longitudinal axis due to the convex outer surfaces 110, 114 of the first and second leg members 102, 104. The general symmetry of the surgical clip 100 may facilitate engagement with a clip applier.

The inner portion 116 and the outer portion 118 may be separated by at least one transverse aperture or channel 124 extending between the side surfaces of the second leg member 104 to enable compression of the second leg member 104. For example, the channel 124 may enable the inner portion 116 to be resiliently compressed toward the outer portion 118 and distribute load along the length of the tissue, while more effectively gripping and retaining the tissue within the surgical clip 100. In some embodiments, the inner portion 116, the outer portion 118, and/or the channel 124 may extend greater than a quarter of a length of the second leg member 104. In some embodiments, the inner portion 116, the outer portion 118, and/or the channel 124 may extend greater than half of a length of the second leg member 104. In some embodiments, the inner portion 116, the outer portion 118, and/or the channel 124 may extend substantially the entire length of first leg member 102. The outer portion 118 may have a width and/or thickness less than the inner portion 116 to increase flexibility and reduce constraint of the flexibility of the inner portion 116 as the inner portion 116 flexes and flattens during closing and/or latching. The inner portion 116 and the outer portion 118 may be formed integrally of the same material (e.g., injection molded into a polymer) to facilitate manufacturing.

The hinge member 106 may be resiliently flexible and integrally formed with the first and second leg members 102, 104. The hinge member 106 may have a concave inner surface and a convex outer surface. The concave inner surface of the hinge member 106 may join the inner surface 108 of the first leg member 102 and the inner surface 112 of the second leg member 104. The convex outer surface of the hinge member 106 may join the first outer surface 110 of the first leg member 102 and the second outer surface 114 of the second leg member 104. The hinge member 106 may also include a curved slot located between hinge surfaces to increase flexibility of the hinge member 106.

The surgical clip 100 may also include a latching mechanism having one or more interlocking or latching elements. For example, the first leg member 102 may transition to a hook member 126 at its distal portion, and the second leg member 104 may transition to a tip member 128 at its distal portion. A distal portion of the hook member 126 may curve inwardly and point generally toward the concave inner surface of the hinge member 106. The hook member 126 may have one or more transverse beveled surfaces and a concave inner surface which merges with the inner surface 108 to define a latching recess. The tip member 128 may be V-shaped defining a slot configured to receive the beveled surfaces, as the hook member 126 deflects around the tip member 128. The hook member 126 and the tip member 128 may engage to form the latching mechanism. For example, the latching recess may engage with the tip member 128 in the course of compressing the surgical clip 100 into the closed configuration (e.g., FIG. 1B) secured around a vessel or other tissue.

Figure 4:
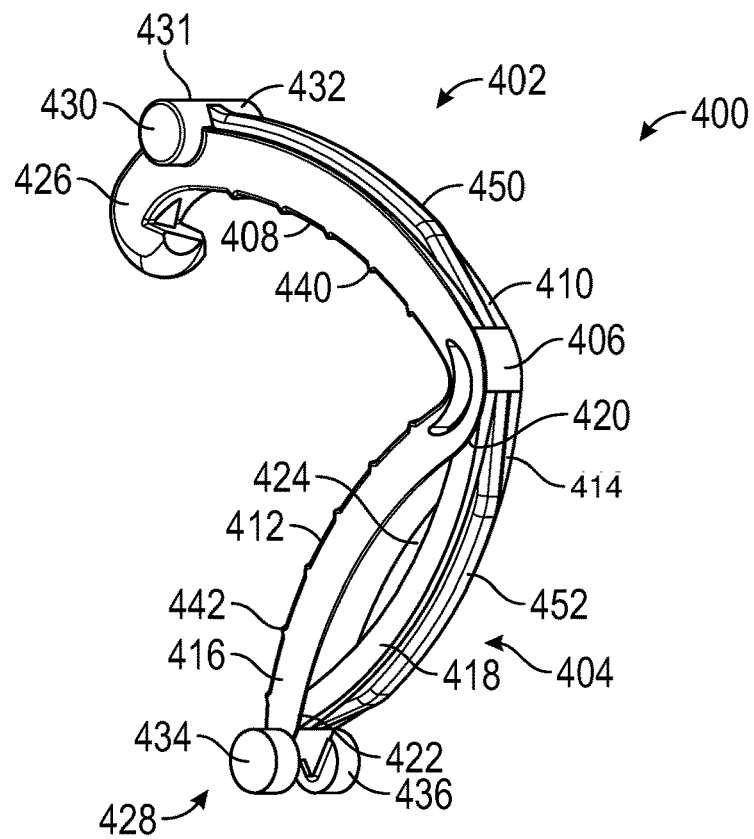
FIG. 4 illustrates a perspective view of a second exemplary embodiment of a surgical clip in an exemplary open configuration according to the present disclosure.

The leg members 102, 104 may include one or more bosses 130-136 along the length to engage jaw members of the clip applier. For example, the first leg member 102 may include bosses 130, 132 protruding perpendicular to each of opposing side surfaces adjacent to the distal portion of the first leg member 102 and immediately proximal of the hook member 126. In the illustrated example of the surgical clip 100, the bosses 130, 132 may be cylindrical and project outwardly beyond the side surfaces of the first leg member 102. The bosses 130, 132 may also be coupled together by a bridge portion (431, shown in FIG. 4). The second leg member 104 may also include bosses 134, 136 at the distal portion of the second leg member 104. The bosses 134, 136 may be cylindrical and protrude perpendicular to each of opposing side surfaces of the second leg member 104, extending longitudinally distal of the point of tip member 128. The bosses 134, 136 may be separated by the V-shaped slot of the tip member 128 (e.g., as illustrated in FIG. 4). The jaw members of the clip applier may engage the bosses 130-136 and pivot the leg members 102, 104 about the hinge member 106 to compress the surgical clip 100 into a closed and/or latched configuration around a vessel.

The surgical clip 100 may include at least one first tooth 140 positioned on the inner surface 108 of the first leg member 102, and at least one second tooth 142 positioned on the inner surface 112 of the second leg member 104. For example, the surgical clip 100 may include a plurality of first teeth 140 positioned on the inner surface 108 of the first leg member 102, and a plurality of second teeth 142 positioned on the inner surface 112 of the second leg member 104.

Figure 2A:
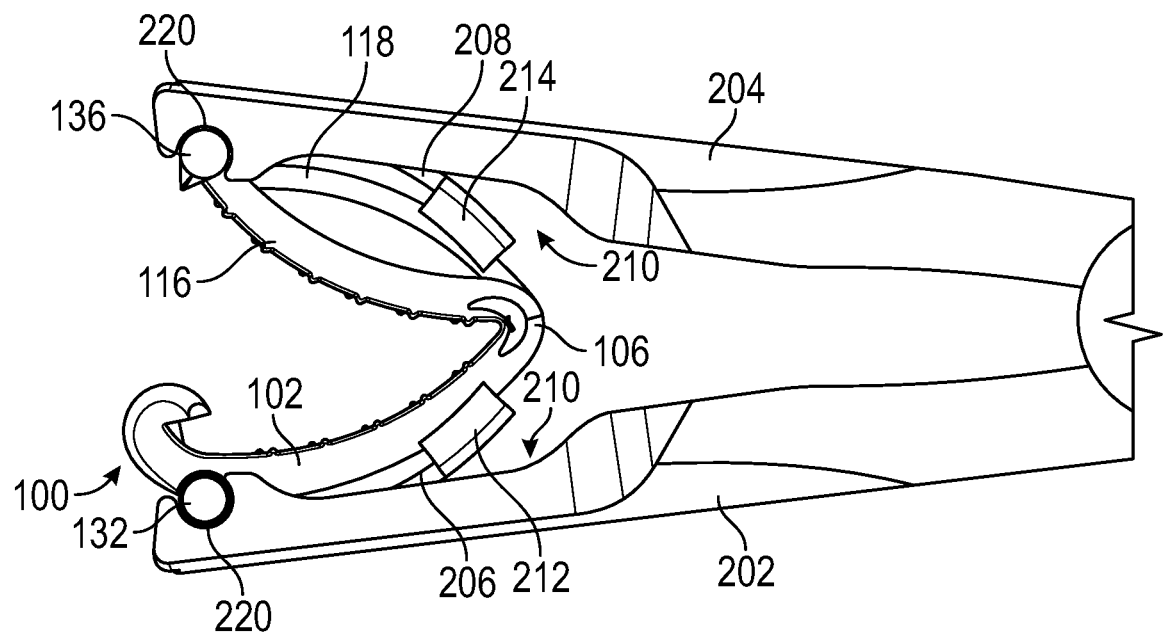
FIG. 2A illustrates a side view of a first exemplary embodiment of a manual clip applier loaded with the surgical clip of FIGS. 1A-B.
Figure 2B:
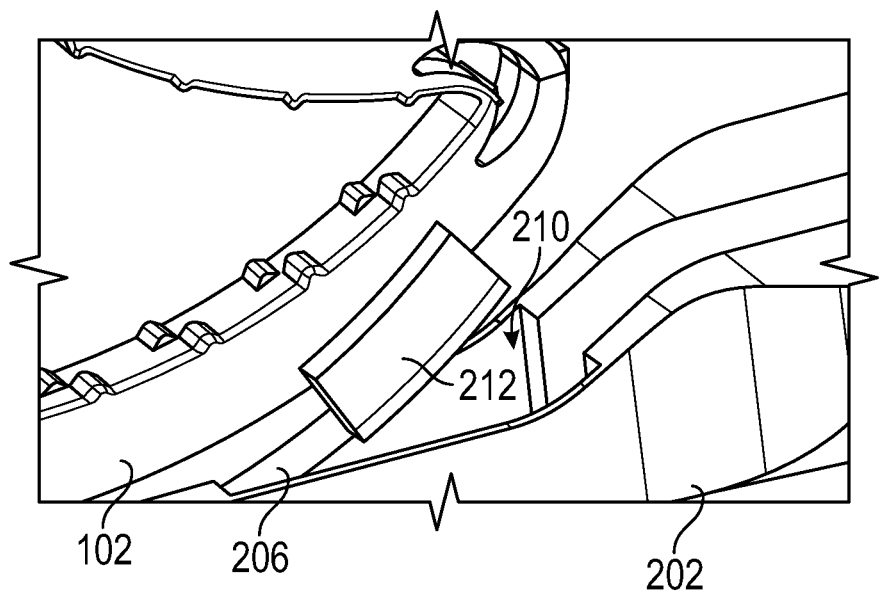
FIG. 2B illustrates a perspective view of the exemplary manual clip applier and surgical clip of FIG. 2A.

FIGS. 2A-B illustrate a manual clip applier 200 loaded with the surgical clip 100. As depicted, the clip applier 200 may include a first jaw member 202 and a second jaw member 204 pivotably coupled to each other to close and/or latch the surgical clip 100 onto tissue. The first jaw member 202 may be configured to receive and/or engage the outer surface 110 of the first leg member 102, and the second jaw member 204 may be configured to receive and/or engage the outer surface 114 of the second leg member 104. As illustrated, the first jaw member 202 may include a first flexible member 206 configured to receive and/or engage the outer surface 110 of the first leg member 102, and the second jaw member 204 may include a second flexible member 208 configured to receive and/or engage the outer surface 114 of the second leg member 104.

Figure 5A:
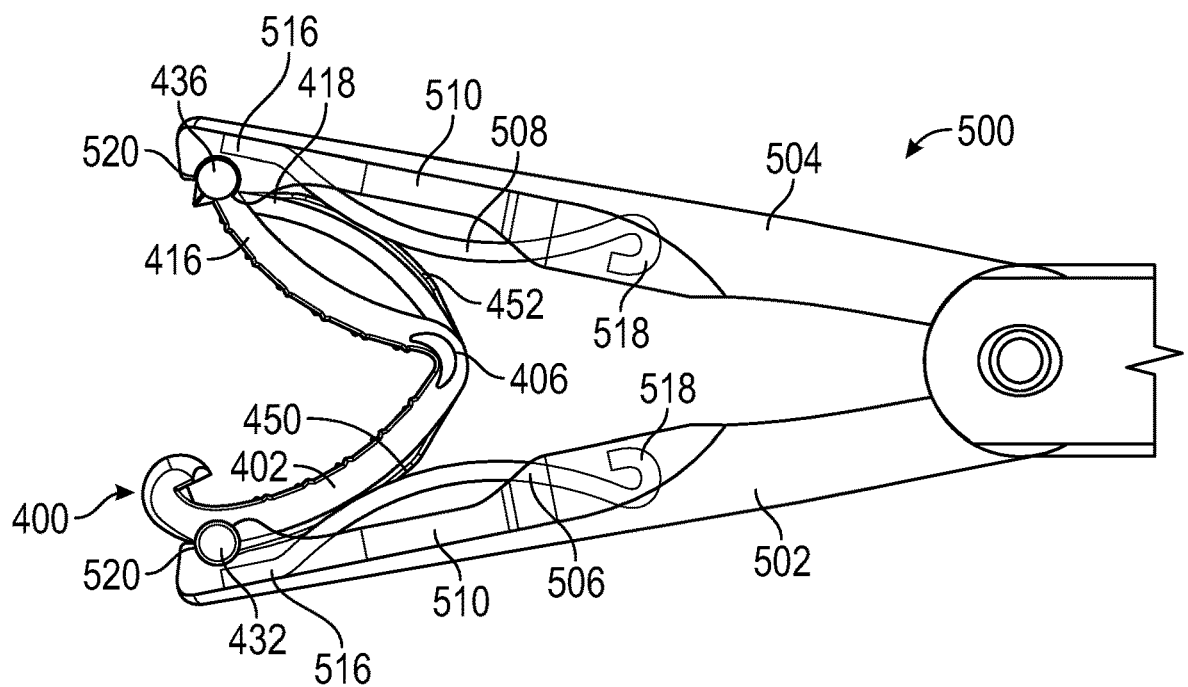
FIG. 5A illustrates a side view of a second exemplary embodiment of a manual clip applier loaded with the surgical clip of FIG. 4.
Figure 5B:
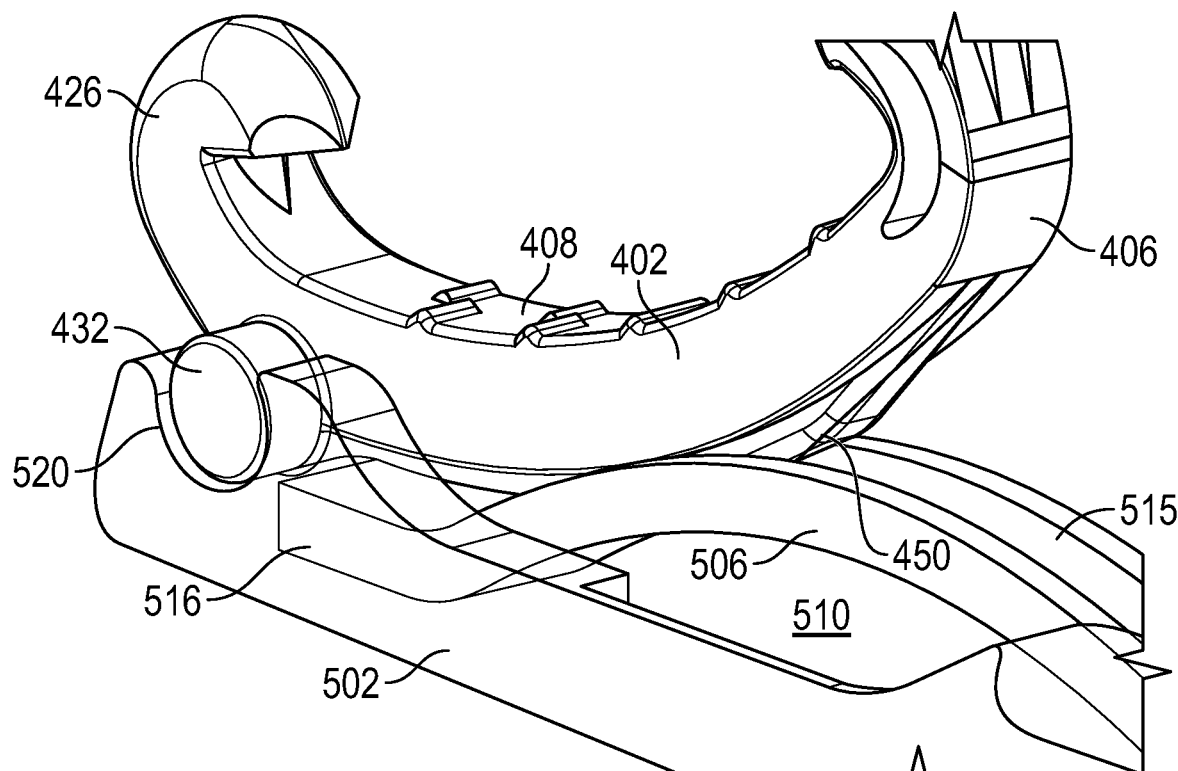
FIG. 5B illustrates a perspective view the exemplary manual clip applier and surgical clip of FIG. 5A.
Figure 5C:
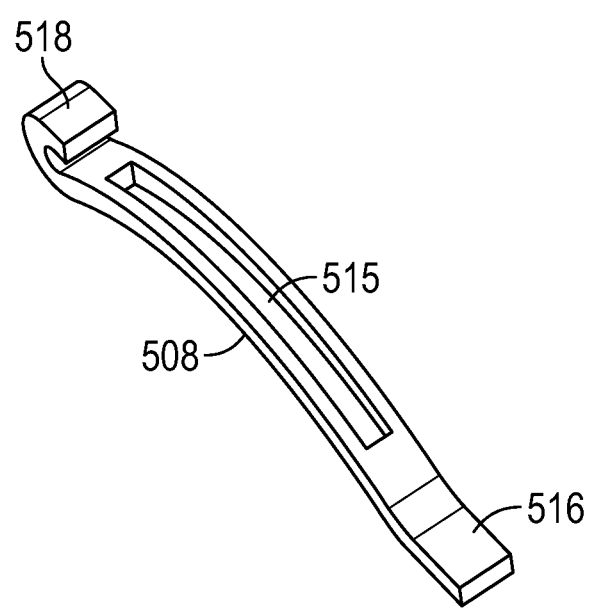
FIG. 5C illustrates a perspective view an exemplary embodiment of a flexible member of the manual clip applier of FIGS. 5A-B.

The flexible members 206, 208 may have a distal portion (e.g., 516, as illustrated in FIGS. 5A-C) secured or fixed (e.g., welded) to a distal portion of the respective first and second jaw members 202, 204. The distal portions of the flexible members 206, 208 may be received in a longitudinal channel 210 on an inner portion of the respective jaw member 202, 204. The proximal portions of the flexible members 206, 208 may be free from any direct attachment to the clip applier 200 and be spaced apart. The flexible members 206, 208 may be a spring-based metal (e.g., spring steel) that is biased to receive and/or engage the leg members 102, 104 of the surgical clip 100. The flexible members 206, 208 may have an arcuate shape when the first and second jaw members 202, 204 are in an open configuration. The flexible members 206, 208 may be configured to deflect and/or straighten as the first and second jaw members 202, 204 close the surgical clip 100. For example, as the first and second jaw members 202, 204 close the surgical clip 100, the flexible members 206, 208 may deflect radially outward toward the respective jaw members 202, 204 and/or straighten longitudinally (lengthen) to accommodate the deflection of the surgical clip 100 and the approximation of the first and second jaw members 102, 104.

The flexible members 206, 208 may each include a retention member 212, 214 on a proximal portion configured to laterally stabilize the first and second leg members 102, 104. As illustrated, the retention members 212, 214 may each include first and second opposing sidewalls configured to receive the leg member 102, 104 and prevent or reduce lateral movement of the surgical clip 100. Each of the retention members 212, 214 may be integrally formed with the respective flexible member 206, 208. As further illustrated in FIG. 2B, the longitudinal channel 210 of each of the first and second jaw members 202, 204 may have a narrower portion configured to receive the narrower distal portion of the flexible members 206, 208 and a wider portion configured to receive the width of the retention members 212, 214 as the first and second jaw members 202, 204 approximate and/or close. Therefore, the flexible members 206, 208 may be configured to nest into the first and second jaw members 202, 204, as the clip applier 200 closes the surgical clip 100.

The flexible members 206, 208 may engage and/or receive the surgical clip 100 throughout the closure and/or locking of the surgical clip 100.

The clip applier 200 may also include features on the distal portion of each of the first and second jaw members 202, 204 configured to secure distal portions of the first and second leg members 102, 104. For example, as illustrated, each of the first and second jaw members 202, 204 may include at least one groove 220 configured to receive the bosses 130-136 of the surgical clip 100. As further illustrated in FIGS. 6B and 7B, each of the first and second jaw members 202, 204 may have first and second grooves 220 separated by the channel 210 and configured to receive the bosses 130-136.

Figure 3:
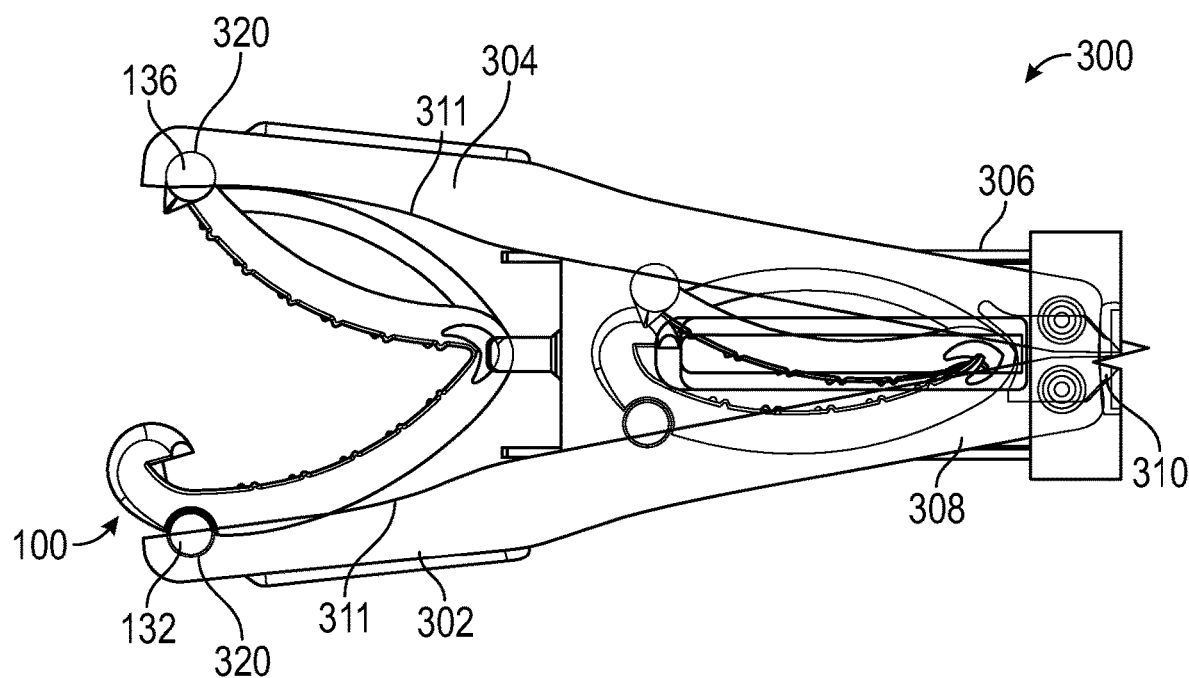
FIG. 3 illustrates a side view of an exemplary embodiment of an automatic clip applier loaded with the surgical clip of of FIGS. 1A-B.

FIG. 3 illustrates an automatic clip applier 300 loaded with one or more of the surgical clips 100. The clip applier 300 may include first and second jaw members 302, 304 configured to close and/or lock the surgical clip 100 around tissue.

As further illustrated, the clip applier 300 may include an elongated shaft 306 having a channel 308 in communication with the first and second jaw members 302, 304. The clip applier 300 may further include a feeder 310 configured to advance the surgical clip 100 from a supply (e.g., cartridge) through the the channel 308 to a position between first and second jaw members 302, 304. The generally symmetric outer surfaces 110, 114 of the surgical clip 100 may provide a favorable fit in the channel 308 to align the surgical clip 100 in a vertical direction. The outer portion 118 of the second leg member 104 may facilitate advancement of the surgical clip 100 by contacting an inner surface of the elongated shaft 306, stabilizing the surgical clip 100 in a vertical direction. The fit of the surgical clip 100 may eliminate the need of a pinky finger on a distal end of the feeder 310, which is designed to prevent relative movement of the surgical clip 100 in a vertical direction. The convex outer surfaces of the surgical clip 100 may further increase the surface area engaged by the first and second jaw members 302, 304 to provide more uniform compression along the length of the surgical clip 100 during closure of the first and second jaw members 302, 304.

The clip applier 300 may also include features on the distal portion of each of the first and second jaw members 302, 304 configured to secure distal portions of the first and second leg members 102, 104. For example, as illustrated, each of the first and second jaw members 302, 304 may include at least one groove 320 configured to receive the bosses 130-136 of the surgical clip 100. The outer surfaces 110, 114 of the surgical clip 100 may also be received in concave inner surfaces 311 of the first and second jaw members 302, 304 to facilitate feeding of the bosses 130-136 from the channel 308 into the grooves 320.

FIG. 4 illustrates a perspective rear view of a surgical clip 400. The surgical clip 400 may have similar features as the surgical clip 100 (FIGS. 1A-B). Similar reference numbers may refer to like parts of the surgical clip 100.

As illustrated, the surgical clip 400 may have a proximal portion and a distal portion. The surgical clip 400 may further include a first leg member 402 having a proximal portion and a distal portion, and a second leg member 404 having a proximal portion and a distal portion. The first and second leg members 402, 404 may be integrally joined at the proximal portions by a hinge member 406.

The first and second leg members 402, 404 may include surfaces having curved portions. For example, the first leg member 402 may include a first inner surface 408 and a first outer surface 410, and the second leg member 404 may include a second inner surface 412 and a second outer surface 414. The first inner surface 408 may have a concave curvature, and the first outer surface 410 may have a convex curvature. The second inner surface 412 may have a convex curvature, and the second outer surface 414 may have a convex curvature. The inner surfaces 408, 412 may be approximated or contact in a closed configuration. The first leg member 402 may also include opposing side surfaces, and the second leg member 404 may include opposing side surfaces.

The second leg member 404 may include an inner portion 416 (e.g., an inner rib) and an outer portion 418 (e.g., an outer rib) integrally joined at a proximal portion 420 and a distal portion 422. The inner portion 416 may form at least a portion of the second inner surface 412 and an outer surface with a concave curvature, and the outer portion 418 may form at least a portion of the second outer surface 414 and have an inner surface with a concave curvature. The curvature of the inner portion 416 and/or outer portion 418 may extend from a proximal end (e.g., the proximal portion 420) to a distal end (e.g., distal portion 422). At least one of the inner portion 416 and the outer portion 418 may have a thickness less than a thickness of the first leg member 402. The smaller thickness of the inner portion 416 and/or outer portion 418 may provide more flexibility to allow deflection of the second inner surface 412 to different thicknesses of tissue. The inner portion 416, the outer portion 418, and/or the first leg member 402 may have substantially the same radius of curvature. The surgical clip 400 may have a generally symmetric outer profile along the longitudinal axis due to the convex outer surfaces 410, 414 of the first and second leg members 402, 404. The general symmetry of the surgical clip 400 may facilitate engagement with a clip applier.

The inner portion 416 and the outer portion 418 may be separated by at least one transverse aperture or channel 424 extending between side surfaces of the second leg member 404 to enable compression of the second leg member 404. For example, the channel 424 may enable the inner portion 416 to resiliently compress toward the outer portion 418 and distribute load along the length of the tissue, while more effectively gripping and retaining the tissue within the surgical clip 400. In some embodiments, the inner portion 416, the outer portion 418, and/or the channel 424 may extend greater than a quarter of a length of the second leg member 404. In some embodiments, the inner portion 416, the outer portion 418, and/or the channel 424 may extend greater than half of a length of the second leg member 404. In some embodiments, the inner portion 416, the outer portion 418, and/or the channel 424 may extend substantially the entire length of first leg member 402. The outer portion 418 may have a width and/or thickness less than the inner portion 416 to increase flexibility and reduce constraint of the flexibility of the inner portion 416 as the inner portion 416 flexes and flattens during closing and/or latching. The inner portion 416 and the outer portion 418 may be formed integrally of the same material (e.g., injection molded of a polymer to facilitate manufacturing.

The outer surface 410 of the first leg member 402 may include a longitudinal protrusion 450, and the outer surface 414 of the second leg member 404 may include a longitudinal protrusion 452. The longitudinal protrusions 450, 452 may engage and/or be received by the clip applier to prevent lateral movement of the surgical clip 400. The longitudinal protrusion 450, 452 may extend substantially the entire length of the respective outer surface 410, 414.

The hinge member 406 may be resiliently flexible and integral to the first and second leg members 402, 404. The hinge member 406 may have a concave inner surface and a convex outer surface. The concave inner surface of the hinge member 406 may join the inner surface 408 of the first leg member 402 and the inner surface 412 of the second leg member 404. The convex outer surface of the hinge member 406 may join the first outer surface 410 of the first leg member 402 and the second outer surface 414 of the second leg member 404. The hinge member 406 may also include a curved slot located between hinge surfaces to increase flexibility of the hinge member 406.

The surgical clip 400 may also include a latching mechanism having one or more interlocking or latching elements. For example, the first leg member 402 may transition to a hook member 426 at its distal portion, and the second leg member 404 may transition to a tip member 428 at its distal portion. A distal portion of the hook member 426 may curve inwardly and point generally toward the concave inner surface of the hinge member 406. The hook member 426 may have one or more transverse beveled surfaces and a concave inner surface which merges with the inner surface 408 to define a latching recess. The tip member 428 may be V-shaped defining a slot configured to receive the beveled surfaces, as the hook member 426 deflects around the tip member 428. The hook member 426 and the tip member 428 may engage to form the latching mechanism. For example, the latching recess may engage with the tip member 428 in the course of compressing the surgical clip 400 into the closed configuration secured around a vessel or other tissue.

The leg members 402, 404 may include one or more bosses 430-436 along the length to engage jaw members of the clip applier. For example, the first leg member 402 may include bosses 430, 432 protruding perpendicular to each of opposing side surfaces adjacent to the distal portion of the first leg member 402 and immediately proximal of the hook member 426. In the illustrated example of the surgical clip 400, the bosses 430, 432 may be cylindrical and project outwardly beyond the first outer surface 410 of first leg member 402. The bosses 430, 432 may also be coupled together by a bridge portion 431. The second leg member 404 may also include bosses 434, 436 at the distal portion of the second leg member 404. The bosses 434, 436 may be cylindrical and protrude perpendicular to each of opposing side surfaces of the second leg member 404, extending longitudinally distal of the point of tip member 428. The bosses 434, 436 may be separated by the V-shaped slot of the tip member 428. The jaw members of the clip applier may engage the bosses 430-436 and pivot the leg members 402, 404 about the hinge member 406 to compress the surgical clip 400 into a closed and/or latched configuration around a vessel.

The surgical clip 400 may include at least one first tooth 440 positioned on the inner surface 408 of the first leg member 402, and at least one second tooth 442 positioned on the inner surface 412 of the second leg member 404. For example, the surgical clip 400 may include a plurality of first teeth 440 positioned on the inner surface 408 of the first leg member 402, and a plurality of second teeth 442 positioned on the inner surface 412 of the second leg member 404.

FIGS. 5A-C, 6A-B, and 7A-B illustrate various embodiments of manual clip appliers 500, 600, 700 (hereinafter, 500-700) configured to apply the surgical clip 400. (Although illustrated with the surgical clip 400, it should be readily understand that the clip appliers 500-700 may, additionally or alternatively, be used with the surgical clip 100.) As illustrated, the clip applier 500-700 may include a first jaw member 502-702 and a second jaw member 504-704 pivotably coupled to each other to close and/or latch the surgical clip 400 onto tissue. The first jaw member 502-702 may be configured to receive and/or engage the outer surface 410 of the first leg member 402, and the second jaw member 504-704 may be configured to receive and/or engage the outer surface 414 of the second leg member 404. As illustrated, the first jaw member 502-702 may include a first flexible member 506-706 configured to receive and/or engage the outer surface 410 of the first leg member 402, and the second jaw member 504-704 may include a second flexible member 508-708 configured to receive and/or engage the outer surface 414 of the second leg member 404.

The flexible members 506-706, 508-708 may have a distal portion (e.g., 516, as shown in FIGS. 5A-C) secured or fixed (e.g., welded) to a distal portion of the respective first and second jaw members 502-702, 504-704. The distal portions of the flexible members 506-706, 508-708 may be received in a longitudinal channel 510-710 on an inner portion of the respective jaw member 502-702, 504-704. In some embodiments, as illustrated in FIGS. 5A-C, the flexible members 506, 508 may have a free proximal portion 518. The proximal portions 518 may be free from any direct attachment to the clip applier 200 and spaced apart. The proximal portion 518 may be received in the longitudinal channel 510 and have a curved or curled tip to reduce friction when the proximal portion 518 translates as the flexible member 506, 508 deflects and/or straightens. In some embodiments, as illustrated in FIGS. 6A-B, the proximal portions of the flexible members 606, 608 may be joined or welded at a joint 620. In some embodiments, as illustrated in FIGS. 7A-B, the proximal portions of the flexible members 706, 708 may be integrally formed with a bend 722.

The flexible members 506-706, 508-708 may be a spring-based metal (e.g., spring steel) that is biased to receive and/or engage the leg members 402, 404 of the surgical clip 400. In some embodiments, the flexible members 506-706, 508-708 may have an arcuate shape (e.g., FIGS. 5A-5C and 6A-6B) or may be straight (e.g., FIGS. 7A-B) when the first and second jaw members 502-702, 504-704 are in an open configuration. The flexible members 506-706, 508-708 may be configured to deflect radially and/or straighten longitudinally as the first and second jaw members 502-702, 504-704 close the surgical clip 400. For example, as the first and second jaw members 502-702, 504-704 close the surgical clip 400, the flexible members 506-706, 508-708 may deflect radially and/or straighten longitudinally to accommodate the deflection of the surgical clip 400.

The flexible members 506-706, 508-708 may each include a retention member configured to laterally stabilize the first and second leg members 402, 404. As illustrated, the retention members may each include a longitudinal slot or channel 515-715 configured to engage and/or receive the longitudinal protrusions 450, 452 to prevent or reduce lateral movement of the surgical clip 400 during loading, delivery, and/or closing of the surgical clip 400. As further illustrated, the flexible members 506-706, 508-708 may have a reduced, substantially uniform width favorably corresponding to the width of the surgical clip 400. The flexible members 506-706, 508-708 may also be received in the longitudinal channel 510-710 as the first and second jaw members 502-702, 504-704 close onto the surgical clip. The flexible members 506-706, 508-708 may be configured to nest into the first and second jaw members 202, 204, as the clip applier 200 closes the surgical clip 100. Therefore, the flexible members 506-706, 508-708 may engage and/or receive the surgical clip 400 throughout the closure and/or locking of the surgical clip 400. The longitudinal channel 515-715 may be configured to release the longitudinal protrusion 450, 452 when the clip applier 500-700 closes and/or locks the surgical clip 400, and the biasing of the flexible members 506-706, 508-708 may urge the surgical clip 400 away from the jaw members 502-702, 504-704 as the clip applier 500-700 is re-opened.

The clip applier 500-700 may also include features on the distal portion of each of the first and second jaw members 502-702, 504-704 configured to secure distal portions of the first and second leg members 402, 404. For example, as illustrated, each of the first and second jaw members 502-702, 504-704 may include at least one groove 520-720 configured to receive the bosses 430-436 of the surgical clip 400. As further illustrated in FIGS. 6B and 7B, each of the first and second jaw members 502-702, 504-704 may have first and second grooves 520-720 separated by the longitudinal channel 510-710 and configured to receive the bosses 430-436.

The various embodiments of the surgical clips 100, 400 of the present invention may be made of any suitable size and may be applied to any number of tissues, such as blood vessels, lymph nodes, nerves, fallopian tubes, or cardiac tissue. The various embodiments of the surgical clips 100, 400 may be constructed from any suitable biocompatible material, such as metals and polymers. However, the present invention is particularly suitable for practice with polymeric clips. Thus, the various embodiments of the surgical clips 100, 400 preferably consist of a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded, or otherwise processed into like articles.

The many features and advantages of the invention are apparent from the detailed specification. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical clip configured to ligate tissue, the surgical clip comprising:
   a first leg member including a first proximal portion, a first distal portion, a first inner surface, and a first outer surface, and the first outer surface having a convex curvature; and
   a second leg member including a second proximal portion, a second distal portion, a second inner surface, and a second outer surface, the second leg member further including an inner portion and an outer portion integrally formed and separated by an aperture, the aperture extending between first and second side surfaces on opposing lateral sides of the second inner surface, the second inner surface having a convex curvature extending from the second proximal portion to the second distal portion, and the second outer surface being formed on the outer portion and having a convex curvature.

2. The surgical clip of claim 1, wherein the inner portion and the outer portion comprise a polymeric material.

3. The surgical clip of claim 1, wherein the outer portion extends greater than a quarter of a length of the second leg member.

4. The surgical clip of claim 1, wherein the outer portion extends greater than half of a length of the second leg member.

5. The surgical clip of claim 1, wherein a width of the outer portion is smaller than a width of the inner portion.

6. The surgical clip of claim 1, wherein the convex curvature of the second outer surface extends from a proximal end of the outer portion to a distal end of the outer portion.

7. The surgical clip of claim 1, wherein the first outer surface comprises a first longitudinal protrusion, and the second outer surface comprises a second longitudinal protrusion.

8. The surgical clip of claim 1, further comprising a hook member on a distal portion of one of the first and second leg members, and a tip member on another of the first and second leg members, the hook member being configured to receive the tip member in a closed configuration.

9. The surgical clip of claim 1, further comprising a hinge member pivotably coupling the first proximal portion and the second proximal portion.

10. The surgical clip of claim 1, wherein the first inner surface has a concave curvature extending from the first proximal portion to the first distal portion.

11. The surgical clip of claim 1, further comprising: a first boss on the first side surface; and a second boss on the second side surface.

12. The surgical clip of claim 1, wherein the surgical clip is an integral one-piece body.

13. A clip applier system configured to ligate tissue, the clip applier system comprising:
a clip applier comprising a first jaw member and a second jaw member; and
the surgical clip of claim 1 loaded in the clip applier, wherein the first outer surface engages the first jaw member, and the second outer surface engages the second jaw member.

14. The clip applier system of claim 13, wherein the first jaw member comprises a first flexible member configured to engage the first leg member, and the second jaw member comprises a second flexible member configured to engage the second leg member.

15. The clip applier system of claim 14, wherein the first flexible member is biased into engagement with the first outer surface, and the second flexible member is biased into engagement with the second outer surface.

16. The clip applier system of claim 14, wherein a portion of the first flexible member is received within a channel of the first jaw member, and a portion of the second flexible member is received within a channel of the second jaw member.

17. The clip applier system of claim 14, wherein a distal portion of the first flexible member is secured to the first jaw member, and a distal portion of the second flexible member is secured to the second jaw member.

18. The clip applier system of claim 14, wherein a proximal portion of the first flexible member and a proximal portion of the second flexible member are spaced apart.

19. The clip applier system of claim 14, wherein a proximal portion of the first flexible member and a proximal portion of the second flexible member are joined or integral.

20. The clip applier system of claim 13, wherein the first leg member comprises a first longitudinal protrusion configured to be received in a first slot of the first jaw member, and the second leg member comprises a second longitudinal protrusion configured to be received in a second slot of the second jaw member.

21. A surgical clip configured to ligate tissue, the surgical clip comprising:
a first leg member including a first proximal portion, a first distal portion, a first inner surface, and a first outer surface, the first inner surface having a concave curvature and the first outer surface having a convex curvature;
a second leg member including a second proximal portion, a second distal portion, a second inner surface, and a second outer surface, the second leg member further including an inner portion and an outer portion separated by an aperture, the aperture extending between first and second side surfaces on opposing lateral sides of the second inner surface to enable compression of the second leg member, the second inner surface being formed on the inner portion and having a convex curvature extending from the second proximal portion to the second distal portion, and the second outer surface being formed on the outer portion and having a convex curvature, wherein the inner portion and the outer portion are integrally formed of a polymeric material;
a hinge member pivotably coupling the first proximal portion and the second proximal portion;
a hook member on the first distal portion of the first leg member; and
a tip member on the second distal portion of the second leg member, the hook member being configured to extend around the tip member to secure the surgical clip in a closed configuration.

22. The surgical clip of claim 21, further comprising: a first boss on the first side surface; and a second boss on the second side surface.

23. The surgical clip of claim 21, wherein the surgical clip is an integral one-piece body.

24. A surgical clip configured to ligate tissue, the surgical clip comprising:
a first leg member including a first proximal portion, a first distal portion, a first inner surface, and a first outer surface, and the first outer surface having a convex curvature;
a second leg member including a second proximal portion, a second distal portion, a second inner surface, and a second outer surface, the second leg member further including an inner portion and an outer portion integrally formed and separated by an aperture, the aperture extending between first and second side surfaces on opposing lateral sides of the second inner surface to enable compression of the second leg member, the second inner surface having a convex curvature extending from the second proximal portion to the second distal portion, and the second outer surface being formed on the outer portion and having a convex curvature; and
at least one tooth positioned on the second inner surface.

25. The surgical clip of claim 24, further comprising: a first boss on the first side surface; and a second boss on the second side surface.

26. The surgical clip of claim 24, wherein the inner portion and the outer portion comprise a polymeric material.

27. The surgical clip of claim 24, wherein the surgical clip is an integral one-piece body.

* * * * *